(12) United States Patent
Seguin

(10) Patent No.: US 7,094,796 B2
(45) Date of Patent: Aug. 22, 2006

(54) COUPLING PRODUCT BETWEEN TRYPTAMINE AND AN ALPHA-AMINO ACID, PROCESS FOR ITS PREPARATION AS WELL AS ITS APPLICATION IN THE NEUROCOSMETIC FIELD

(75) Inventor: Marie-Christine Seguin, Monaco (MC)

(73) Assignee: Exsymol S.A.M., Monaco (MC)

( * ) Notice: Subject to any disclaimer, the term of this patent is extended or adjusted under 35 U.S.C. 154(b) by 386 days.

(21) Appl. No.: 10/678,706

(22) Filed: Oct. 2, 2003

(65) Prior Publication Data

US 2004/0110814 A1 Jun. 10, 2004

(30) Foreign Application Priority Data

Oct. 4, 2002 (MC) .................................. 002488

(51) Int. Cl.
C07D 403/02 (2006.01)
A61K 31/4164 (2006.01)
(52) U.S. Cl. ...................... 514/397; 514/414; 514/419; 548/312.1; 548/455
(58) Field of Classification Search ................. 514/397, 514/414, 419; 548/312.1, 455
See application file for complete search history.

(56) References Cited

U.S. PATENT DOCUMENTS

| 5,792,784 A | 8/1998 | Seguin et al. | 514/400 |
| 6,046,340 A | 4/2000 | Seguin et al. | 548/335.5 |

FOREIGN PATENT DOCUMENTS

| EP | 1020179 A | 7/2000 |
| FR | 2697843 A1 * | 5/1994 |
| RU | 2217196 C2 | 2/2002 |
| WO | WO 9419325 A | 1/1994 |
| WO | WO 9512581 A | 11/1995 |
| WO | WO 0072815 A | 7/2000 |
| WO | WO 03072124 A | 4/2003 |

OTHER PUBLICATIONS

Search Report (Mar. 1, 2004) from French Patent Application 0215741 (Rapport De Recherche Préliminaire, INPI Institute National de la Propriete Industrielle).

Search Report (Mar. 1, 2004) from European Patent Application 03022092 (Rapport De Recherche Europeenne, Office européen des Brevets).

Patricia Melnyk et al.: "A new diastereoselective synthesis of cis 1-aminoindoloquinolizidine" *Tetrahedron Letters*, vol. 34, No. 32, 1993, pp. 5085-5088.

Mueller, J. Constanze D., et al.: "Non-peptidic cysteine derivatives as inhibitors of matrix metalloproteinases" *Biological Chemistry*, vol. 378, No. 12, (1997), pp. 1475-1480.

Jean-Francois Nicolay, Isabelle Imbert: "Targeting the cutaneous nervous network" *Cosmetics & Toiletries*, vol. 118, No. 7, (2003) pp. 37-40, 42, 44.

* cited by examiner

Primary Examiner—Kamal A. Saeed
(74) Attorney, Agent, or Firm—Drinker Biddle & Reath LLP; Daniel A. Monaco

(57) ABSTRACT

The purpose of the invention concerns a family of pseudo-dipeptides which are coupling products between tryptamine, an indole-primary amine, and a selection of alpha-amino acids, the said pseudodipeptides having the following general formula (I):

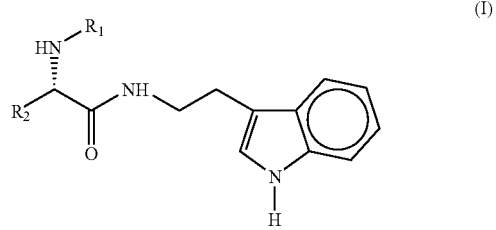

in which:
  $R_1$ represents a hydrogen atom, an acyl or acyloxy radical,
  $R_2$ represents the side chain of an alpha-amino acid chosen among L-glutamic acid, L-arginine, L-cysteine, L-methionine, L-histidine, L-tryptophan, L-tyrosine.

The present invention also concerns the process for the preparation of said products as well as their applications in neurocosmetic compositions or as active substances on the cutaneous nervous system.

9 Claims, No Drawings

COUPLING PRODUCT BETWEEN TRYPTAMINE AND AN ALPHA-AMINO ACID, PROCESS FOR ITS PREPARATION AS WELL AS ITS APPLICATION IN THE NEUROCOSMETIC FIELD

The present invention relates to a pseudodipeptide family, coupling products between tryptamine which is an indole-primary amine, and a selection of alpha-amino acids.

The purpose of the invention also concerns the process for the preparation of said products as well as their applications as active substances on the cutaneous nervous system.

Interactions between nervous system and cutaneous cells, both on anatomical and functional aspects, are numerous and now well-established. Besides, this recent understanding enlarged to new activity fields, particularly in cosmetic so-called "neurocosmetic" that describes any action aiming to act on such interactions, and therefore to cure any linked cutaneous cosmetic impairment or disorder.

Skin is indeed a highly innervated organ. The innervation is dense and fine in the dermic layers, but is also up to the most supercifial ones located in epidermis, except for stratum corneum. Our sensorial system such as touch, pain, itching, temperature, pression, etc is notably based on this innervation.

Connections between nerves and skin are thus highly linked and are characterized, in addition to physical contacts, by a permanent exchange of information between nervous cells and cutaneous cells. The mecanisms inducing this so-called "neurogenic" communication are now well known.

These exchanges are first of all the result of biologically active substances called neuromediators (Lotti T. and al., J. Am. Acad. Dermatol. (1995), vol.33, pp.482–496). Most of these chemical vehicules of nervous information found within the derm and the epidermis are from peptidic origin: substance P, neuropeptide Y, calcitonin gene-related peptide or CGRP, etc . . . . But others belong to catecholamine group with especially adrenaline and acetylcholine. Moreover these exchanges also result from the existence of neuromediator-specific receptors on the surface of skin cells, nervous or not. When these receptors are activited by the neuromediators, they modulate the properties of cutaneous cells, both epidermic ones (keratinocytes, melanocytes, Langerhans cells) and dermic ones (fibroblasts, endothelial cells).

Generally speaking, a strong implication of the nervous system in cutaneous metabolisms is now clearly accepted. All main skin functions, such as immunity, body defense against damaging effects from the external medium, cell differentiation and proliferation, pigmentation, are likely today to be modulated and even controlled by the nervous system (L. Misery, International Journal of Cosmetic Science (2002), vol.24, pp.111–116).

At skin level and from its role within the immune mecanism for instance, an impairment of cutaneous nervous system after a damaging effect of a located foreign body comes with an abnormal inflammatory reaction. Indeed, cutaneous neuropeptides secreted by the nerve endings participate to the mecanisms of this inflammatory reaction by acting on the receptors located on the immune cells' membranes (lymphocytes, macrophages) and/or cutaneous (keratinocytes, melanocytes, fibroblasts, Langerhans cells) in order to liberate cytokines. These latter are necessary for the induction, the maintenance or the reduction of the inflammatory state. The "substance P" neuropeptide is so described as being an activator of the synthesis of cytokines (IL-1 or TNF-alpha) (Ansel J. C and al., Journal of Investigative Dermatology Symposium Proceedings (1997), vol.2, pp.23–26).

Another neuropeptide, the CGRP or 'calcitonin gene-related peptide', is considered more as a stimulator of the keratinocytes' proliferation (Takahashi K. and al., J. Invest. Dermatol. (1993), vol.101, pp.646–651).

Consequently, it is today perceived all the interest to intercede with nervous cells in cutaneous biology. Potential applications of such an implication are therefore numerous in cosmetology. New perspectives are notably proposed in the treatment of certain skin impairments such as the cutaneous neurodegeneration, the inflammatory and irritation phenomena, problems of desquamation, cutaneous ageing and dryness, healing, face dermatosis, excessive sweating, etc (L. Misery, International Journal of Cosmetics Science (2002), vol.24, pp.111–116 and cited references).

The applicant has therefore considered an approach aiming to act on some biological functions of the skin which involve the nervous system, but exclusively in a local way. As a matter of fact, nerve endings of skin are exclusively targeted and not the central nervous system like numerous therapeutic applications. Also an action on cerebral level accompanied by a cutaneous impact is not considered at all.

For that purpose, the applicant decided on the use of an active ingredient type, suitable in cosmetic, with a structure close to natural neurogenic substances which are identified for governing the interactions between nerve endings and cutaneous cells, and are able to interfere with these cutaneous nervous communications. The applicant has also considered a cosmetic disorder induced by a situation of stress or growth factors' deprivation, displayed and detailed hereafter in the specification of the invention.

The applicant thus chose a structure with peptidic nature or similar to it by analogy with neuromediators found in the skin, and more specifically with neuropeptides. For this, a panel of natural alpha-amino acids peculiar to constitute a neuropeptide has been chosen. Among this panel, the applicant selected a type of amino acids with polar or apolar side chain, as well as with metal-chelating behaviour and anti-oxidant activity. (Ahmad M. M. and al., JAOCS (1993), vol. 80, pp.837–840), (Gopala Krishna A. G. and al., JAOCS (1994), vol.71, pp.645–647), Popov I. and al., Luminescence (1999), vol.14, pp.169–174), because of the oxidative nature of numerous stresses which are responsible for cutaneous impairment and because of obtained results by the applicant with some selected amino acids after displaying neurocosmetic properties. At last, in order to target the active ingredient towards the nervous cell, the applicant has also selected the presence of an indole group since there are some membrane receptors present to the nervous cells' surface whose affinity for this type of molecular group is today known.

The purpose of the present invention is therefore a family of pseudodipeptides resulting from the coupling between tryptamine which is a primary amine with an indole core, and a selection of alpha-amino acids, the said pseudodipeptides having the following general formula (I):

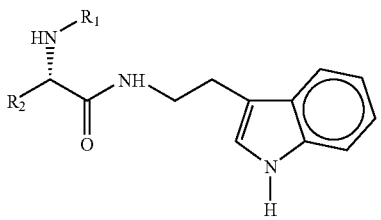

(I)

in which:
R₁ represents a hydrogen atom, an acyl or acyloxy radical,
R₂ represents the side chain of an alpha-amino acid chosen among L-glutamic acid, L-arginine, L-cysteine, L-methionine, L-histidine, L-tryptophan, L-tyrosine.

It has to note that when R₁ represents an acyl or acyloxy radical which are biodegradable substituents that can be hydrolyzed in vivo, the corresponding derivatives constitute precursor forms of the targeted pseudodipeptides, with a lipophilic character peculiar to promote their cutaneous penetration, and thus to improve their bio-availability after topical application of said pseudopeptide.

According to an embodiment of the invention, the applicant quotes the alpha-L-glutamyltryptamine, L-methionyltryptamine and L-tryptophantryptamine pseudodipeptides, the prefered example being the alpha-L-glutamyltryptamine.

In the case of the alpha-L-glutamyltryptamine pseudodipeptide, the invention also concerns an analog with the same properties than this latter, and resulting from the conversion of the glutamic radical in a pyroglutamic radical according to an intramolecular cyclisation well-known by the state of the art (Burstein Y. and al., Proc. Natl. Acad Sci. USA (1976), vol.73, pp.2604–2608) and the person skilled in the art.

Another prefered embodiment of the invention is the pseudodipeptide having the general formula (I) in which R₁ represents an acetyl or ter-butyloxycarbonyl radical, and R₂ represents the side chain of an alpha-amino acid chosen among L-glutamic acid, L-methionine and L-tryptophan.

As far as we know to date, structures targeted by the applicant are new since they have never been disclosed. The prior state of the art however discloses similar structures, but never for the hereabove purposes nor considered approach.

The literature discloses a certain number of aminoacyl derivatives of an amine called "biogenic" with an indole characteristic : the serotonin or 5-hydroxytryptamine, which is synthetized in the organism. This primary amine issued from hydroxylation and decarboxylation steps of tryptophan essential amino acid is both a chemical mediator in the central nervous system and a neurohormone secreted into blood and urinary circulations (Vigy M., Conc. Med. (1969), vol.14, pp.2865–2868). This amine is involved in several fields (Hindle A. T., Br. J. Anaesth (1994), vol.73, pp.395–407) and more specifically in the mechanism of various psychiatric troubles (nervous breakdown, schizophrenia, anxiety,etc) as well as in some neurologic pathologies such as Alzheimer disease or migraine.

In order to decrease the neurotoxicity associated to its pharmacological use but also the multiplicity of its effects, some amino acids residues have been conjugated to the serotonin or its methoxylated analog. It is thus described the synthesis of L-Gly-5-hydroxytryptamine, beta-L-Ala-5-hydroxytryptamine, gamma-L-aminobutyryl-5-hydroxytryptamine, L-Met-5-hydroxytryptamine, alpha-L-Glu-5-hydroxytryptamine, L-Cyst-5-hydroxytryptamine (Suvorov N. N. and al., Bioorg. Khim. (1976), vol.2, pp.729–736), the synthesis of L-Gly-5-methoxytryptamine, alpha-L-Ala-5-methoxytryptamine, beta-L-Ala-5-methoxytryptamine, gamma-L-Glu-5-methoxytryptamine, L-Arg-5-methoxytryptamine, L-Val-5-methoxytryptamine, L-Meth-5-methoxytryptamine, L-Trp-5-methoxytryptamine, L-Cyst-5-methoxytryptamine (Popova G. V. and al., Tr. Mosk. Khim. Tekhnol. Inst. im D I Mendeleeva (1977), vol.94, pp.84–98), the synthesis of alpha-L-Glu-5-methoxytryptamine (Popova G. V. and al., Zh. Obshch. Khim. (1979), vol.49, pp.1418–1424). In the above compounds, and also later on, the amino acid residues involved in the bond with the primary amine are represented by their three letter code according to the hereafter nomenclature:

| Gly | glycine |
| Ala | alanine |
| Met | methionine |
| Glu | glutamic acid |
| Arg | arginine |
| Val | valine |
| Trp | tryptophan |
| Cyst | cysteine |

The SU 296409 patent is related to the preparation of serotonin and 5-methoxytryptamine peptidic derivatives. The document reports some radioprotecting properties for all those structures.

The alpha-methyltryptamine is another serotonin analog also known for a long time. Medically studied as a potential anti-depressant (Mashkovskii M. D. and al., Psikhiatr. (1963), n°1, pp.72), it was marketed in the sixties in USSR under the name of Indopan®. It was claiming, in addition to an anti-depressive activity, a stimulating action on the central nervous system with notably a stimulation of the motor activity as well as the excitability of reflexes. But always with the aim to modulate the undesirable properties of alpha-methyltryptamine, it has then been introduced an amino acid residue on the side chain of the amine, especifically the glutamic acid (Vigdorchik M. M. ands al., Pharm. Chem. J. (1977), vol.11, pp.305–309). The pharmacological properties of alpha-L-glutamyl-DL-alpha-methyltryptamine have been then compared to the ones with Indopan®.

The alpha-ethylated glutamic homolog was also synthetized (Bulatova N. N. and al., Khim. Farm. Zh. (1968), vol.2, pp.6–9), and its action on the central nervous sytem was compared to the one of the alpha-L-glutamyl-DL-alpha-methyltryptamine.

The applicant is not at all in the situation of this prior art, namely a direct action on the central nervous system, nor in the situation of an improvement of pharmacological properties of serotonin or alpha-methyltryptamine indoleamines by a better tolerance and a longer effect. With a totally different approach, the applicant considered the synthesis of an active substance able, with regard to its structural analogy with cutaneous neuromediators, to display an affinity for receptors of nervous and cutaneous cells in order to induce the neurocosmetic properties described hereafter with the presentation of tests.

In the state of the art, the identification of glutamylamines including the glutamyltryptamine has also been noted in the *Aplysia california* marine mollusc. In all cases, it has only been isolated then chemically reproduced glutamic derivatives conjugated in gamma position with tryptamine, hydroxytryptamine, dopamine, octopamine, tyramine and phenylethylamine amines (Mc Caman M. W. and al., J. Neurochem. (1985), vol.45, 1828–1835). The gamma-glutamylation step of said amines is supposed to inactivate these amines.

Among products having the general formula (I), examples hereafter constitute a non-restrictive list of pseudodipeptides according to the invention:

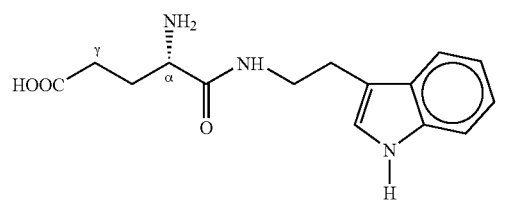

alpha-L-glutamyltryptamine
(alpha-L-Glu-Tryp)

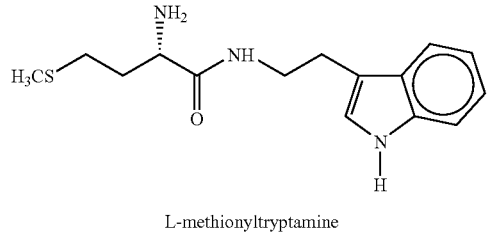

L-methionyltryptamine
(L-Met-Tryp)

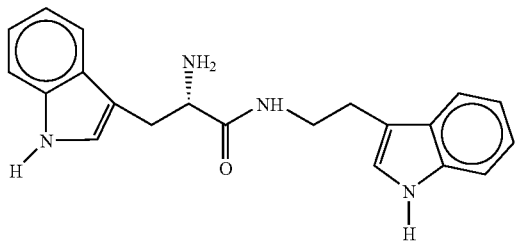

L-tryptophantryptamine
(L-Trp-Tryp)

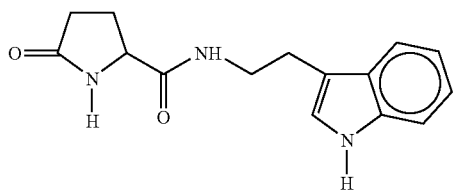

L-pyroglutamyltryptamine
(L-pGlu-Tryp)

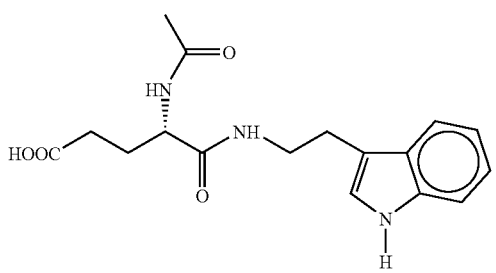

N-acetyl-alpha-L-glutamyltryptamine
(N-Ac-alpha-L-Glu-Tryp)

-continued

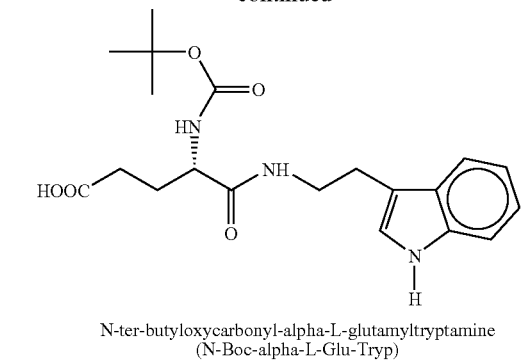

N-ter-butyloxycarbonyl-alpha-L-glutamyltryptamine
(N-Boc-alpha-L-Glu-Tryp)

The present invention also concerns a chemical process developed for the preparation of pseudodipeptides which are purposes of the invention. It has successively the following steps:

The first step consists in protecting the alpha-amino function of the L-aminoacid with an acyl or acyloxy radical, preferentially with acetyl or terbutyloxycarbonyl radicals.

In the case of glutamic acid, the protection step of the alpha-amino function is immediately followed by an esterification step of the gamma-carboxylic function with an alkyl radical, preferentially with ter-butyl radical.

The second step of the process consists in coupling the N-protected L-aminoacid and, gamma-O-esterified in the case of the L-glutamic acid, with tryptamine. This coupling is carried out either directly with a typical coupling agent, preferentially the N,N'-dicyclohexylcarbodiimide, or via the previous activation or in situ of the alpha-carboxylic function of the N-protected aminoacid by action of a typical activator, preferentially the hydroxybenzotriazol. The "typical", phrase means an agent well-known for the person skilled in the art.

In a third step, optional according to the seeked pseudodipeptide, the N-protecting group of the pseudodipeptide resulting from the hereabove mentioned step is removed, advantageously by acidolysis and preferentially with an aqueous solution of hydrochloride solution.

The invention has also as purpose neurocosmetic compositions containing, as active substance, a pseudodipeptide having the general formula (I), preferentially the alpha-L-glutamyltryptamine, in combination with one or several appropriated cosmetically excipients.

A last purpose of the invention relates to the neurocosmetic use of pseudodipeptides according to the invention. This use outcomes from properties displayed hereafter demonstrating the ability of said pseudodipeptides to interact with cutaneous nervous cells.

The applicant thus demonstrated the use of pseudodipeptides according to the invention successively:

as neurocosmetic agent displaying a cytoprotecting effect, alternatively designated neuroprotecting, towards cutaneous nervous cells which are submitted to an ultraviolet radiation, as neurocosmetic agent intended for slowing down the neurodegeneration process, as neurocosmetic agent intended for fighting against the neurogenic inflammation, and as neurocosmetic agent able to stimulate the cutaneous immune cells.

The cell model chosen by the applicant in all its in vitro experimentations was a pheochromocytomal cell line with murine origin, called "PC 12" and commonly accepted for neurobiological and neurochemical studies on nervous cells (Greene L. A. and al., Proc. Natl. Acad. Sci. USA (1976), vol.73, pp.2424–2428), in particular on peripheral neurones which innervate skin (Keilbaugh S. A., Biochem. Pharm. (1997), vol.53, pp.1485–1492).

The PC 12 line was used after differentiation according to a method described in the literature (Greene L. A. et al. in Culturing Nerve Cells (1991), MIT Press, Cambridge, Mass., pp.207–225).

The following tests illustrate above-mentioned properties or effects.

Test 1: cytoprotecting effect of the alpha-L-glutamyltryptamine, L-methionyltryptamine and L-tryptophantryptamine on PC 12 cells submitted to a UV-B stress. Comparison with a reference antioxidant. A cytotoxic UV-B stress is applied on the nervous cell model (285 nm±5; 500 mJ/cm$^2$), in the absence then in the presence of active ingredient, successively the alpha-L-glutamyltryptamine (Glu-Tryp), L-methionyltryptamine (Met-Tryp) and L-tryptophantryptamine (Trp-Tryp).

The cell death is then evaluated by the measure of lactico-dehydrogenase activity (LDH) in the culture medium. This activity is proportional to the cell lysis which follows the cell death.

The results are expressed in % of protection and are given by the ratio of LDH activity according to the following equation:

$$\% \text{ of protection} = \frac{LDH_{treated\ cells} - LDH_{non\ treated\ control\ cells}}{LDH_{non\ treated\ control\ cells}} * 100$$

The results are compared to the ones obtained with a reference antioxidant which is vitamin E (vit.E).

Validity of the test is checked by the measure of LDH activity in the culture medium of non stressed cells (negative check). Values listed in the tables hereafter are average values obtained from six measures.

Results:

Test 2: anti-aging effect of the alpha-L-glutamyltryptamine, L-methionyltryptamine and L-tryptophantryptamine with the slowdown of the neurodegeneration process of PC 12 submitted to a deprivation of serum.

A deprivation of serum is applied to PC 12 cells in order to imitate the aging effects. The neurodegeneration process is followed, in the absence then in the presence of active ingredient, successively the alpha-L-glutamyltryptamine (Glu-Tryp), L-methionyltryptamine (Met-Tryp) and L-tryptophantryptamine (Trp-Tryp), by a kinetic measure of the release in the culture medium of lactico-dehydrogenase enzyme (LDH).

The results are expressed in relative survival rate given by the LDH activity ratio according to the following equation:

$$\text{survival rate } \% = \frac{LDH_{treated\ aged\ cells} - LDH_{non\ treated\ control\ cells}}{LDH_{non\ treated\ control\ cells}} * 100$$

The values listed in the tables hereafter are average values obtained from six measures after a serum deprivation of nine days.

Results:

|  | Glu-Tryp (0.86 mM) | Glu-Tryp (0.43 mM) | Glu-Tryp (0.1 mM) |
|---|---|---|---|
| improvement of the survival time (%) | +33 | +19 | +19 |
|  | Met-Tryp (0.85 mM) | Met-Tryp (0.48) mM | Met-Tryp (0.1 mM) |
| improvement of the survival time (%) | +28 | +15 | +12 |
|  | Trp-Tryp (0.85 mM) | Trp-Tryp (0.45 mM) | Trp-Tryp (0.1 mM) |
| improvement of the survival time (%) | +30 | +20 | +17 |

|  | Glu-Tryp (1.72 mM) | Glu-Tryp (0.86 mM) | Glu-Tryp (0.43 mM) | Glu-Tryp (0.1 mM) | Glu-Tryp (0.05 mM) | Vit. E (2 mM) |
|---|---|---|---|---|---|---|
| % of protection | 69 | 61 | 48 | 39 | 26 | 34 |
|  | Met-Tryp (1.91 mM) | Met-Tryp (0.85 mM) | Met-Tryp (0.48 mM) | Met-Tryp (0.1 mM) | Met-Tryp (0.05 mM) | Vit. E (2 mM) |
| % of protection | 65 | 53 | 42 | 32 | 20 | 34 |
|  | Trp-Tryp (1.80 mM) | Trp-Tryp (0.85 mM) | Trp-Tryp (0.45 mM) | Trp-Tryp (0.1 mM) | Trp-Tryp (0.05 mM) | Vit. E (2 mM) |
| % of protection | 66 | 58 | 45 | 35 | 22 | 34 |

Test 3: anti-inflammatory effect of the alpha-L-glutamyltryptamine, L-methionyltryptamine and L-tryptophantryptamine on PC 12 cells submitted to a pro-inflammatory stress. Comparison with two controls (PC 12): the first one is non stressed, the second one is stressed but non treated A UV-B pro-inflammatory stress is applied on PC 12 cells (285 nm±5; 150 mJ/cm$^2$), in the absence then in the presence of active ingredient, successively the alpha-L-glutamyltryptamine (Glu-Tryp), L-methionyltryptamine (Met-Tryp) and L-tryptophantryptamine (Trp-Tryp).

The neurogenic inflammatory response is evaluated by the measure of the rate of pro-inflammatory interleukine-6 (IL-6) which are produced by the PC 12 cells.

Results:

|  | non irradiated control | Glu-Tryp (0.86 mM) | Glu-Tryp (0.43 mM) | Glu-Tryp (0.1 mM) | non treated irradiated control |
|---|---|---|---|---|---|
| produced IL-6 rate (pg/ml) | 0 | 70 | 180 | 240 | 400 |

|  | non irradiated control | Met-Tryp (0.85 mM) | Met-Tryp (0.48 mM) | Met-Tryp (0.1 mM) | non treated irradiated control |
|---|---|---|---|---|---|
| produced IL-6 rate (pg/ml) | 0 | 85 | 210 | 290 | 400 |

|  | non irradiated control | Trp-Tryp (0.85 mM) | Trp-Tryp (0.45 mM) | Trp-Tryp (0.1 mM) | non treated irradiated control |
|---|---|---|---|---|---|
| produced IL-6 rate (pg/ml) | 0 | 100 | 210 | 305 | 400 |

Test 4: stimulation of the neuro immuno-cutaneous system with the alpha-L-glutamyltryptamine, L-methionyltryptamine or L-tryptophantryptamine.

Comparison with Two Controls

PC 12 cells are differentiated according to a special protocol to avoid artefacts. After a brief deprivation of growth and differentiation factors, PC 12 are incubated in different concentrations of pseudodipeptides, successively the alpha-L-glutamyltryptamine (Glu-Tryp), L-methionyltryptamine (Met-Tryp) and L-tryptophantryptamine (Trp-Tryp).

After a five days-incubation, the cellular supernatants containing neuromediators and miscellaneous secretions are sampled then introduced in the culture of immune monocyte cells, the THP-1 line.

The effect on the neuro immuno-cutaneous system is observed by measuring the rate of IL-1β interleukines produced by the monocyte cells in response to the addition of supernatants coming from the culture of PC 12 cells.

The results are compared to two controls: the first one with immune cells without supernatant, the second one containing immune cells with supernatant but non treated.

Results:

|  | THP-1 without supernat. | THP-1 + supernat. + Glu-Tryp (0.43 mM) | THP-1 + supernat. + Glu-Tryp (0.1 mM) | THP-1 + supernat. + Glu-Tryp (0.05 mM) | THP-1 + supernat. non treated |
|---|---|---|---|---|---|
| produced IL-1β rate (pg/ml) | 0 | 90 | 63 | 45 | 40 |

|  | THP-1 without supernat. | THP-1 + supernat. + Met-Tryp (0.48 mM) | THP-1 + supernat. + Met-Tryp (0.1 mM) | THP-1 + supernat. + Met-Tryp (0.05 mM) | THP-1 + supernat. non treated |
|---|---|---|---|---|---|
| produced IL-1β rate (pg/ml) | 0 | 85 | 55 | 42 | 40 |

|  | THP-1 without supernat. | THP-1 + supernat. + Trp-Tryp (0.45 mM) | THP-1 + supernat. + Trp-Tryp (0.1 mM) | THP-1 + supernat. + Trp-Tryp (0.05 mM) | THP-1 + supernat. non treated |
|---|---|---|---|---|---|
| produced IL-1β rate (pg/ml) | 0 | 92 | 60 | 44 | 40 |

What is claimed is:

1. A pseudodipeptide of formula (I):

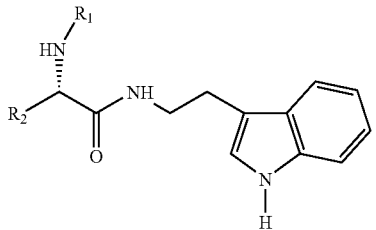

in which:
R$_1$ represents a hydrogen atom, an acyl radical or an acyloxy radical, and
R$_2$ represents the side chain of an alpha-amino acid selected from the group consisting of L-glutamic acid, L-arginine, L-cysteine, L-methionine, L-histidine, L-tryptophan, and L-tyrosine.

2. The pseudodipeptide according to claim 1, selected from the group consisting of alpha-L-glutamyltryptamine, L-methionyltryptamine and L-tryptophantryptamine.

3. The pseudodipeptide according to claim 1, which is alpha-L-glutamyltryptamine.

4. The pseudodipeptide according to the claim 1, wherein R$_1$ represents an acetyl or tert-butyloxycarbonyl radical, and R$_2$ represents the side chain of an alpha-amino acid selected from the group consisting of L-glutamic acid, L-methionine and L-tryptophan.

5. A process for the preparation of a pseudodipeptide according to claim 1 comprising the following steps:
   a) protecting the alpha-amino function of an alpha-L-amino acid with an acyl or acyloxy radical,
   b) coupling the N-protected alpha-L-amino acid to tryptamine, and
   c) optionally removing the N-protecting group.

6. The process according to claim 5, wherein the L-alpha amino acid is glutamic acid and step a) is followed prior to step b) with the step of esterifying the gamma-carboxylic function of said glutamic acid with an alkyl radical.

7. The process according to claim 5, in which the N-protecting group is acetyl or ter-butyloxycarbonyl.

8. A neurocosmetic comprising a pseudodipeptide according to claim 1, in combination with one or more cosmetically appropriate excipients.

9. A method of protecting cutaneous nervous cells from the cytotoxic effects of ultra-violet radiation comprising administering to an individual or to cutaneous nervous cells from an individual a pseudodipeptide according to claim 1.

* * * * *